(12) United States Patent
Salit et al.

(10) Patent No.: US 8,837,540 B2
(45) Date of Patent: Sep. 16, 2014

(54) SIMPLE, LOW POWER MICROSYSTEM FOR SATURATION SPECTROSCOPY

(75) Inventors: Kenneth Salit, Plymouth, MN (US); Jeff A. Ridley, Shorewood, MN (US); Mary K. Salit, Plymouth, MN (US); Jennifer S. Strabley, Maple Grove, MN (US); Jeffrey Kriz, Eden Prairie, MN (US)

(73) Assignee: Honeywell International Inc., Morristown, NJ (US)

( * ) Notice: Subject to any disclaimer, the term of this patent is extended or adjusted under 35 U.S.C. 154(b) by 414 days.

(21) Appl. No.: 13/325,392

(22) Filed: Dec. 14, 2011

(65) Prior Publication Data

US 2013/0003059 A1    Jan. 3, 2013

Related U.S. Application Data

(60) Provisional application No. 61/502,728, filed on Jun. 29, 2011.

(51) Int. Cl.
 *H01S 3/04* (2006.01)

(52) U.S. Cl.
 USPC ............................................ 372/34; 356/311

(58) Field of Classification Search
 CPC .................... G01N 21/3504; G01N 2021/317; H01S 3/1303; H01S 3/1305
 USPC .................................................. 356/311, 300
 See application file for complete search history.

(56) References Cited

U.S. PATENT DOCUMENTS

| 7,649,189 | B2 | 1/2010 | Cole |
| 7,786,808 | B2 | 8/2010 | DeNatale |
| 2005/0007118 | A1 | 1/2005 | Kitching et al. |
| 2006/0022761 | A1 | 2/2006 | Abeles et al. |
| 2011/0187464 | A1 | 8/2011 | Youngner et al. |
| 2011/0187465 | A1 | 8/2011 | Youngner et al. |
| 2011/0187466 | A1* | 8/2011 | Youngner et al. ............. 331/94.1 |
| 2011/0188524 | A1 | 8/2011 | Youngner et al. |

OTHER PUBLICATIONS

Toptica, "Compact Doppler Free Spectrocopy Unit", "Photonicals Laser Diodes & Laboratory tools", 1998, pp. 1-5, Publisher: Toptica.
Grosswasser et al, "Retroreflecting polarization spectroscopy enabling miniaturization", "Review of Scientific Instruments", Sep. 3, 2009, pp. 1-3, vol. 80, No. 093103.
Kitching et al, "Miniature vapor-cell atomic-frequency references", "Applied Physics Letters", Jul. 15, 2002, pp. 553-555, vol. 81, No. 3, Publisher: Amercian Institute of Physics.

(Continued)

*Primary Examiner* — Tuan Nguyen
(74) *Attorney, Agent, or Firm* — Fogg & Powers LLC

(57) ABSTRACT

A spectroscopic assembly is provided. The spectroscopic assembly includes a thermal isolation platform, a gas reference cell encasing a gas and attached to the thermal isolation platform, the gas reference cell having at least one optically-transparent window, and at least one heater configured to raise a temperature of the encased gas. When a beamsplitter is configured to reflect a portion of an input optical beam emitted by a laser to be incident on the at least one optically-transparent window of the gas reference cell, the reflected portion of the input optical beam is twice transmitted through the gas. When a detector is configured to receive the optical beam twice transmitted through the gas, a feedback signal is provided to the laser to stabilize the laser.

20 Claims, 8 Drawing Sheets

(56) References Cited

OTHER PUBLICATIONS

Knappe, "A microfabricated atomic clock", "Applied Physics Letters", Aug. 30, 2004, pp. 1460-1462, vol. 85, No. 9, Publisher: American Institute of Physics.

Knappe, "Atomic Vapor Cells for Miniature Frequency References", "Proceedsing of the 2003 IEEE International Frequency Control Symposium and PDA Exhibition Jointly with the 17th European Frequency and Time Forum", May 4, 2003, pp. 31-32.

Knappe et al., "Microfabricated saturated absorption laser spectrometer", "Optics Express", May 14, 2007, pp. 6293-6299, vol. 15, No. 10, Publisher: OSA.

Liew et al., "Microfabricated alkali atom vapor cells", "Applied Physics Letters", Apr. 5, 2004, pp. 2694-2696, vol. 84, No. 14, Publisher: American Institute of Physics.

Paul L. Stubbs, "Laser Locking with Doppler-free Saturated Absorption Spectroscopy.", "Laser Locking with Doppler-free Saturated Absorption Spectroscopy.", May 12, 2010, pp. 1-10, Publisher: W&M Quantum Optics Group.

\* cited by examiner

US 8,837,540 B2

SIMPLE, LOW POWER MICROSYSTEM FOR SATURATION SPECTROSCOPY

GOVERNMENT LICENSE RIGHTS

This invention was made with Government support under W31P4Q-09-C0348 awarded by AMRDEC. The Government has certain rights in the invention.

This application claims the benefit of U.S. Provisional Application No. 61/502,728, filed on Jun. 29, 2011, which is incorporated herein by reference in its entirety.

BACKGROUND

Saturation spectroscopy is a well-known technique with a variety of uses. In many applications it is used to compare the frequency of a laser to the frequency of an atomic transition in a dilute gas. For instance, in general the frequency of a laser is not fixed, but will drift due to thermal effects, aging, and other time dependent processes. Some applications (such as cold atom devices, including atomic clocks) require that the laser frequency be controlled by a feedback system to prevent this drift.

SUMMARY

The present application relates to a spectroscopic assembly. The spectroscopic assembly includes a thermal isolation platform, a gas reference cell encasing a gas and attached to the thermal isolation platform, the gas reference cell having at least one optically-transparent window, and at least one heater configured to raise a temperature of the encased gas. When a beamsplitter is configured to reflect a portion of an input optical beam emitted by a laser to be incident on the at least one optically-transparent window of the gas reference cell, the reflected portion of the input optical beam is twice transmitted through the gas. When a detector is configured to receive the optical beam twice transmitted through the gas, a feedback signal is provided to the laser to stabilize the laser.

DRAWINGS

In accordance with common practice, the various described features are not drawn to scale but are drawn to emphasize features relevant to the present invention. Like reference characters denote like elements throughout figures and text.

DETAILED DESCRIPTION

In the following detailed description, reference is made to the accompanying drawings that form a part hereof, and in which is shown by way of illustration specific illustrative embodiments in which the invention may be practiced. These embodiments are described in sufficient detail to enable those skilled in the art to practice the invention, and it is to be understood that other embodiments may be utilized and that logical, mechanical and electrical changes may be made without departing from the scope of the present invention. The following detailed description is, therefore, not to be taken in a limiting sense.

The embodiments of spectroscopy assembly described and shown herein are simple, low power microsystems for saturation spectroscopy. These microsystems for saturation spectroscopy provide a stable spectroscopic signal for feedback to a laser in order to stabilize the frequency of the optical beam emitted by the laser. The feedback system compares the laser frequency to the frequency of an atomic transition using a gas reference cell and a technique known as saturation spectroscopy to generate a feedback signal. In some applications, the laser frequency is compared to the atomic frequency for the purpose of measuring forces (such as magnetic or electric field) which can shift the atomic frequency, or for the purpose of identifying the gas or properties of the gas such as pressure and temperature. In some applications, dilute gas is used to modulate a laser in a controllable way. In that case, external forces are applied to modulate the interaction of the gas and the laser as a means of controlling the laser frequency or amplitude. The embodiments of spectroscopy assembly described herein advantageously require very low power and are robust to misalignment. Some embodiments described herein include a miniature gas reference cell. Previous attempts to miniaturize saturation spectroscopy negatively impacted the spatial mode of the laser beam being stabilized, making the prior art miniaturized saturation spectroscopy unsuitable for some applications, such as miniature atomic clocks. The described embodiments of spectroscopy assemblies with miniature gas reference cells use a minimum number of optical components, and have little or no effect on the optical beam that is provided to an external system.

Figure 1A:
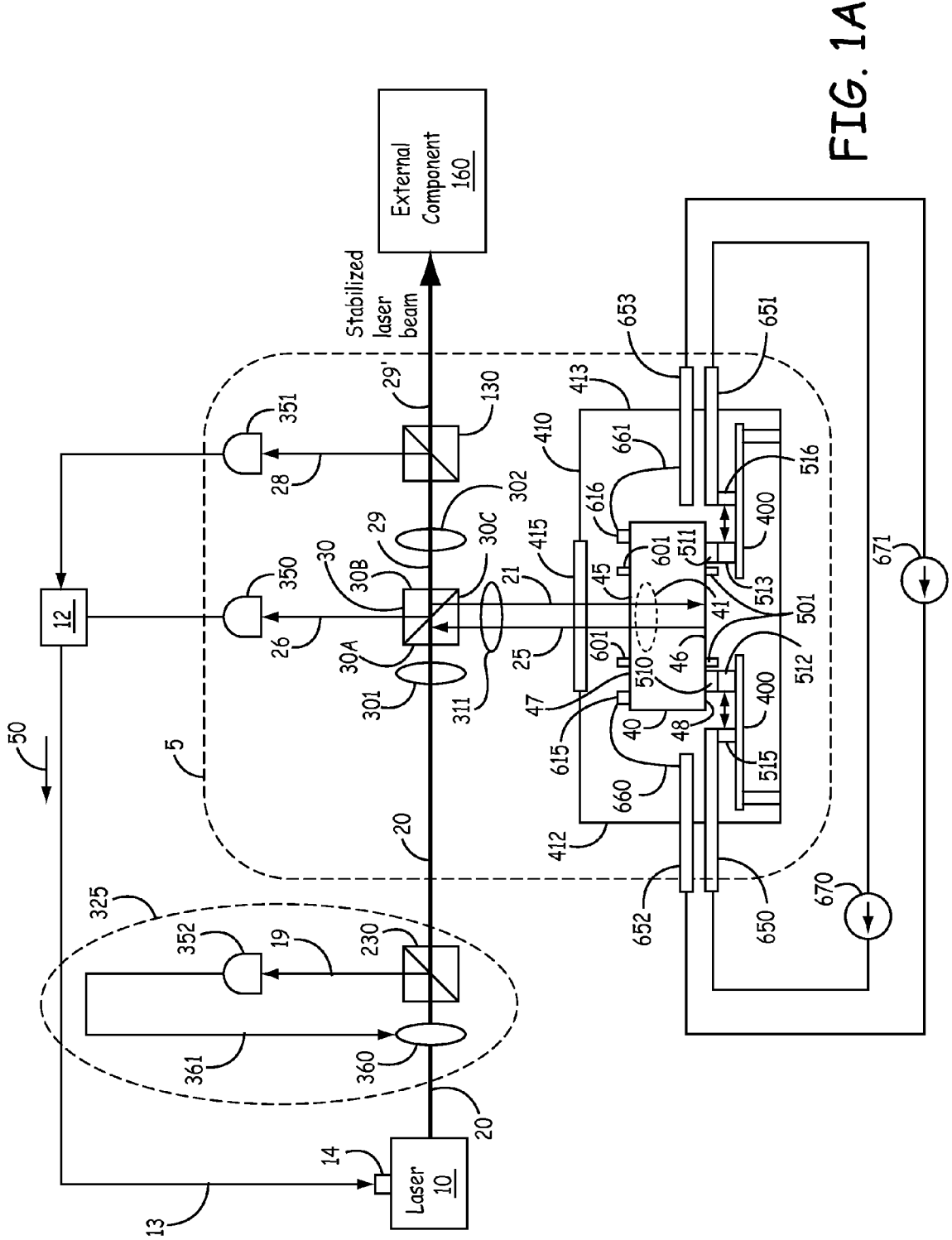
FIG. 1A is a block diagram of an embodiment of a spectroscopy assembly, a laser, and an external component in accordance with the present invention.

FIG. 1A is a block diagram of an embodiment of a spectroscopy assembly 5, a laser 10, and an external component 160 in accordance with the present invention. The spectroscopy assembly 5 shown in FIG. 1A is aligned to provide feedback to lock the laser 10 to a selected frequency. Laser 10 is stabilized by a feedback signal output from the spectroscopic assembly 5 to a laser driver 14 via link 13. The spectroscopic assembly 5 includes a housing 410, a thermal isolation platform 400, and a gas reference cell 40, which encases a gas 41. The thermal isolation platform 400 and the gas reference cell 40 are housed in the housing 410. The housing 410 is also referred to herein as a chip carrier, or a leadless chip carrier (LCC). The gas reference cell 40 is also referred to herein as a "miniature rubidium reference cell 40", "reference cell 40", "vacuum packed cell 40", and "cell 40".

The gas reference cell 40 is supported by at least one thermal isolation platform 400 (also referred to herein as a "scaffold", "first scaffold", and "second scaffold"). At least one heater 601 or 501 is configured to raise the temperature of the encased the gas 41. Specifically, the at least one heater is patterned on at least one of the first optically-transparent window, the second optically-transparent window, a first surface of the gas reference cell, a second surface of the gas reference cell, a portion of the thermal isolation platform adjacent to the first optically-transparent window, and a portion of the thermal isolation platform adjacent to the second optically-transparent window. The thermal isolation platforms 400 ensures the heaters 501 and 601 only heat the gas 41 in the gas reference cell 40 and do not heat (or minimally heat) the housing 410. If the heater is configured on a portion of the thermal isolation platform 400, the thermal isolation platform 400 is configured to impede the flow of heat from the heater to the housing 410 and to permit the flow of heat from the heater to the gas reference cell 40. This selective heat flow can be provided by designing the thermal isolation platform 400 with materials of appropriate thermal conductivity. Since the heat from the heaters 501 and 601 is not transferred to the housing 410, the heaters 501 and 601 operate at low power.

The housing 410 has a transparent window 415 to transmit an input optical beam 21 and an output optical beam 25. The housing 410 is configured for sealing under vacuum. The vacuum in the housing 410 also ensures the heaters 501 and 601 heat only the gas 41 in the gas reference cell 40 and do not heat (or minimally heat) the housing 410. This also helps to minimize the power required by the heaters 501 and 601. In one implementation of this embodiment, the housing 410 is a ceramic housing 410. In another implementation of this embodiment, the spectroscopic assembly 5 is a miniature spectroscopic assembly 5 and the gas reference cell 40 is a miniature gas reference cell 40. The heaters 501 and 601 require very low power if the gas reference cell 40 is miniature gas reference cell 40.

The gas reference cell 40 has a first surface 47 and an opposing second surface 48 configured to encase the gas 41. The first surface 47 has a first optically-transparent window 601 and the second surface 48 has a second optically-transparent window 46. At least one heater 501 or 601 is patterned on the first surface 47 or the second surface 48 of the gas reference cell 40, respectively, or at least one heater is positioned on a respective at least one scaffold to raise the temperature of the encased the gas 41. In one implementation of this embodiment, at least one heater 601 or 501 is patterned on the first optically-transparent window 45 or the second optically-transparent window 46, respectively, to raise a temperature of the encased gas 41. In yet another implementation of this embodiment, only one of the heaters 501 or 601 is used to heat the gas 41. In yet another implementation of this embodiment, the first surface 47 is a glass plate that is the first optically-transparent window 45. In yet another implementation of this embodiment, the second surface 48 is a glass plate that is the second optically-transparent window 46, and the two plates are anodically bonded to a silicon wafer with a cavity, such that the gas is sealed in the cavity. In yet another implementation of this embodiment, the gas reference cell 40 is a single blow-glass mass rather than multiple plates of glass.

Figure 1B:
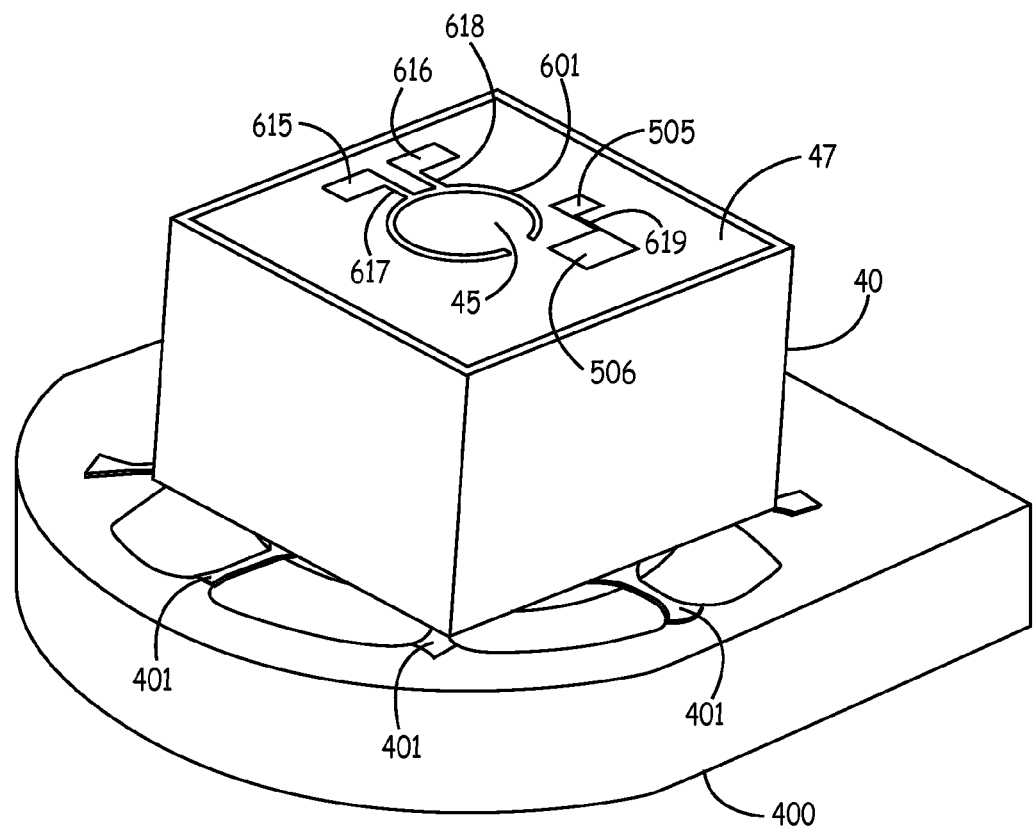
FIG. 1B is an expanded view of a first heater on a first surface of a gas reference cell in the spectroscopic assembly of FIG. 1A.

FIG. 1B is an expanded view of a first heater 601 and a temperature sensor 505 patterned on a first surface 47 of a gas reference cell 40 in the spectroscopic assembly 5 of FIG. 1A in one implementation of this embodiment. The first optically-transparent window 45 is seen in FIG. 1B with the first heater 601 patterned directly on the first optically-transparent window 45. The first heater 601 is shown as a trace line outlining a double partial circle. Electrical-contact pads 615 and 616 are connected with respective trace lines 617 and 618 to the first heater 601. The optical beam 21 (FIG. 1A) is normally incident (or approximately normally incident) on the first optically-transparent window 45 inside the partial circle of the first heater 601. In one implementation of this embodiment, the first heater 601 is patterned on the first surface 47 adjacent to the first optically-transparent window 45.

The gas reference cell 40 optionally includes at least one temperature sensor 505 with a respective at least one electrical-contact pad 506 patterned on the first surface 46 of the gas reference cell 40. The electrical-contact pad 506 is connected with trace line 619 to the temperature sensor 505. In another implementation of this embodiment, the at least one temperature sensor 505 is patterned on the first optically-transparent window 45. In one implementation of this embodiment, the temperature sensors 505 are resistive temperature sensors 505. In one implementation of this embodiment, there are no temperature sensors 505 on the gas reference cell 40.

In one implementation of this embodiment, the second heater 501 (FIG. 1A) is patterned directly on the second optically-transparent window 46. In another implementation of this embodiment, the second heater 501 is patterned on the second surface 48 adjacent to the second optically-transparent window 46. In yet another implementation of this embodiment, the second heater 501 is the same shape as the first heater 301 shown in FIG. 1B. Other shapes for the first heater 601 and second heater 501 are possible. In another implementation of this embodiment, there is no first heater 601 and the second heater 501 is the only heater on the gas reference cell 40. In yet another implementation of this embodiment, there is no second heater 501 and the first heater 601 is the only heater on the gas reference cell 40.

The first heater 601 and the second heater 501 are formed from any conductive material suitable for deposition on the thermal isolation platform 400. In one implementation of this embodiment, the first heater 601 and the second heater 501 are resistive heaters. The electrical-contact pads 506, 615, and 616 and the trace lines 617, 618, and 619 are formed from any conductive material suitable for deposition on the gas reference cell 40.

The gas reference cell 40 is positioned on scaffolding features 401 of the thermal isolation platform 400 to suspend the gas reference cell 40. The narrow scaffolding features 401 minimize the conduction of heat from the heated gas reference cell 40 to the housing 410. In one implementation of this embodiment, the thermal isolation platform 400 is formed from silicon. In another implementation of this embodiment, the thermal isolation platform 400 is formed using microelectro-mechanical system (MEMS) fabrication techniques known to one skilled in the art.

In one embodiment, a heater is fabricated onto the scaffold 400, and heat is transferred to the gas reference cell 40 through solder or an adhesive. In this embodiment, the heater on the scaffold is used, either in conjunction with or instead of, the heater on the first surface 47 of the gas reference cell 40, and/or the heater on the second 48 surface 48 of the gas reference cell 40. In yet another embodiment a second scaffold is attached to the second surface of the gas reference cell 40, and a heater is fabricated onto the second scaffold. In this latter embodiment, the heater on the second scaffold is used, either in conjunction with or instead of, a heater on the first scaffold, a heater on the first surface 47 of the gas reference cell 40, and/or a heater on the second 48 surface 48 of the gas reference cell 40. Thus, embodiments of the spectroscopy assembly include a heater patterned on at least one of the first optically-transparent window, the second optically-transparent window, a first scaffold adjacent to the first optically-transparent window, and a second scaffold adjacent to the second optically-transparent window.

Embodiments of the spectroscopy assembly include a temperature sensor 505 patterned on at least one of the first optically-transparent window 45, the second optically-transparent window 46, a first surface of the gas reference cell 47, a second surface of the gas reference cell 48, a portion of the thermal isolation platform 400 adjacent to the first optically-transparent window 45, and a portion of the thermal isolation platform 400 adjacent to the second optically-transparent window 46.

The gas reference cell 40 is attached to at least one thermal isolation platform 400. When the gas reference cell 40 is operationally positioned on the thermal isolation platform 400, the electrical-contact pads 510 and 511 electrically contact the electrical-contact pads 512 and 513, respectively, in order to provide current to the second heater 501. Likewise, when the gas reference cell 40 is operationally positioned on the thermal isolation platform 400, the electrical-contact pads 506-A and 506-B electrically contact the electrical-contact pads 552 and 553, respectively, in order to sense current in the resistive temperature sensors 505. An opening in the center of thermal isolation platform 400 permits the portion of the optical beam 21 that is transmitted through the second optically-transparent window 46 to propagate to any component that is beyond the thermal isolation platform 400. In one implementation of this embodiment, a reflective surface is positioned to reflect a portion of the optical beam 21 that is transmitted through the second optically-transparent window 46 to propagate to any component that is beyond the thermal isolation platform 400.

As shown in FIG. 1A, the electrical-contact pads 512 and 513 on the thermal isolation platform 400 are connected via trace lines (represented generally as double arrows) to respective electrical-contact pads 515 and 516 on the thermal isolation platform 400. The electrical-contact pads 515 and 516 are connected to respective leads 650 and 651. The leads 650 and 651 extend through respective side walls 412 and 413 of the housing 410. Lead lines 660 and 661 (such as wires) connect the respective electrical-contact pads 615 and 616 (FIG. 1B) to respective leads 652 and 653. The leads 652 and 653 extend through respective side walls 412 and 413 of the housing 410. The leads 650 and 651 that extend through side walls 412 and 413 of the housing 410 are used to connect to a current source 670 outside the housing 410 in order to provide the current to the second heater 501. Specifically, the current source 670 is connected to one end the second heater 501 via the electrical lead 650, electrical-contact pad 515, a trace line 527, the contact pad 512, and electrical-contact pad 512 (see FIG. 1A). The current source 670 is connected to the other end the second heater 501 via the electrical-contact pad 511, the contact pad 513, a trace line 527, the contact pad 516 and the electrical lead 651.

The leads 652 and 653 that extend through side walls 412 and 413 of the housing 410 are used to connect to a current source 671 outside the housing 410 in order to provide the current to the first heater 601. In a similar manner, electrical connections from the electrical-contact pads on the thermal isolation platform 400 connect to leads in order to connect the temperature sensors 505 to temperature sensor control/measurement electronics outside of the housing 410.

The electrical connection of one electrical-contact pad to another electrical-contact pad is done by one of the techniques known in the art including, but not limited to, ball-grid attachment and soldering. It is to be understood that the electrical configuration shown is FIG. 1A is an exemplary embodiment and other configurations are possible.

In one implementation of this embodiment, the second surface 48 of the gas reference cell 40 does not include the second optically-transparent window 46 but is a reflective or partially reflective surface. In another implementation of this embodiment, there is a reflective surface positioned on the bottom surface of the housing 400 to reflect the optical beam back to the beamsplitter 30. In such an embodiment, the first optically-transparent window 45 and second optically-transparent window 46 are anti-reflection coated. In yet another implementation of this embodiment, the first optically-transparent window 44 is anti-reflection coated.

The operation of the exemplary spectroscopic assembly 5 to stabilize the laser 10 is now described with reference to FIG. 1A. The laser 10 emits optical beam 20. The term "optical beam" is also referred to herein as "beam". The optical beam 20 emitted by the laser 10 is also referred to herein as "input optical beam 20" since the spectroscopic assembly 5 is positioned to receive, as an input, the optical beam 20 emitted from the laser 10.

The optical beam 20 first passes through an electro-optical (EO) based intensity servo 325 to reduce laser relative intensity noise (RIN). The electro-optical (EO) based intensity servo 325 includes an EO shutter 360, a beamsplitter 230, and a detector 352. The beam 20 passes through the EO shutter 360 and is incident on the beamsplitter 230. A portion of the beam 20 is reflected by the beamsplitter 230 as optical beam 19 toward the detector 325. The detector 352 provides a feedback signal to the EO shutter 360 via link 361. The speed of the EO shutter 360 is adjusted to reduce or eliminate RIN. The electro-optical (EO) based intensity servo 325 is optional. In one implementation of this embodiment, there is no electro-optical (EO) based intensity servo 325 and the beam 20 is incident on the spectroscopic assembly 5.

A portion of the beam 20 is transmitted by the beamsplitter 230 in the electro-optical (EO) based intensity servo 325 as input optical beam 20 toward the spectroscopic assembly 5. The spectroscopic assembly 5 includes the gas reference cell 40, the housing 410, the thermal isolation platform 400, a first beamsplitter 30, and a first detector 350. The gas reference cell 40 is packaged in a vacuum in the housing 410 and attached to the thermal isolation platform 400. The beamsplitter 30, which is positioned outside of the housing 410, reflects a first portion of the optical beam 20, as optical beam 21, to the gas reference cell 40 and transmits a second portion of the optical beam 20, as optical beam 29, from the spectroscopic assembly 5 to an external component 160. In one implementation of this embodiment, the external component 160 is an atomic based device.

Thus, the beamsplitter 30 is configured to: direct a first (reflected) portion of the optical beam 20 (also referred herein as optical beam 21) to the gas reference cell 40; direct a second (transmitted) portion of the optical beam 20 (also referred herein as optical beam 29) from the spectroscopic assembly 5; and direct the optical beam twice transmitted through the gas 41 (also referred herein as optical beam 25) from the gas reference cell 40 to the first detector 350 as optical beam 26. The first detector 350 provides the spectroscopy signal 50 for laser frequency control as feedback to the laser 10 via link 13.

The optical beam 21 reflected from the beamsplitter 30 is incident on the first optically-transparent window 45 of the gas reference cell 40. The optical beam 21 is transmitted through the gas 41, incident on the reflective surface 46 (e.g., second optically-transparent window 46), reflected from the reflective surface 46, and retransmitted through the gas 41. The optical path of the optical beam 21 and 25 are shown to be offset from each other to clearly indicate the optical path of the optical beams 21 and 25. However, when the first optically-transparent window 45 is parallel to the second optically-transparent window 46 and the optical beam 21 is normally incident on the first optically-transparent window 45 of the gas reference cell 40, the optical beams 21 and 25 are overlapping.

The optical beam 25 that has been twice transmitted through the gas 41 is locked to a side or peak of a specific peak of a saturated absorption spectrum of the heated gas 41 using side-locking or peak-locking techniques known to one skilled in the art. The first detector 350 is configured to provide a feedback signal 50 to stabilize the frequency of the optical beam 20 emitted by the laser 10. The feedback signal 50 is indicative of the amplitude of the optical beam 26 that is detected at the first detector 350. The feedback signal 50 is used to adjust the laser driver 14.

In the embodiment of the spectroscopic assembly 5 shown in FIG. 1A, the spectroscopic assembly 5 also includes a first half wave plate 301, a second half wave plate 302, a quarter wave plate 311, a second beamsplitter 130, and a second detector 351. In this embodiment, the first beamsplitter 30 and the second beamsplitter 130 are polarization beamsplitters 30 and 130. The reflected percent and the transmitted percent of an optical beam incident on the polarization beamsplitters 30 and 130 are based on the polarization of the incident optical beam 20 and 29, respectively. The polarization of the incident optical beam 20 is controlled by the half wave plate 301. The polarization of the incident optical beam 29 is controlled by the half wave plate 302.

The first half wave plate 301 has a fast axis (referred to herein as a first fast axis). The first half wave plate 301 is positioned at an input face 30A of the polarization beamsplitter 30. The orientation of the first fast axis with reference to the polarization of the input optical beam 20 is used to control the ratio of the transmitted (second) portion of the optical beam 20 (e.g., the intensity of the optical beam 29) to the reflected (first) portion of the optical beam (e.g., the intensity of the optical beam 21). Thus, the orientation of the first fast axis with reference to the polarization of the input optical beam 20 controls the relative intensity of the optical beam 29 and the optical beam 21. In one implementation of this embodiment, the first beamsplitter 30 reflects 10% of the input optical beam 20 and transmits 90% of the input optical beam 20 so the ratio of the second portion to the first portion of is 90/10.

As shown in FIG. 1A, the reflective surface 46 is the second optically-transparent window 46. In this case, assuming the second optically-transparent window 46 is glass, 4% of the optical beam 21 is reflected from each surface of the second optically-transparent window 46 as optical beam 25. Optical beam 25 propagates back through the gas 41.

The quarter wave plate 311 has a fast axis (referred to herein as a second fast axis). The quarter wave plate 311 is positioned between an output face 30C of the polarization beamsplitter 30 and the first optically-transparent window 45 of the gas reference cell 40. The orientation of the second fast axis with reference to a polarization of the optical beam 21 (e.g., the reflected portion of the input optical beam 20) controls the polarization of the optical beam 25 that has propagated two times through the gas 41. In one implementation of this embodiment, half wave plates 301 and 302, the quarter wave plate 311 are formed in a rigid plate, a polymer sheet, and/or a film.

The half wave plates 301 and 302, the quarter wave plate 311, the second beamsplitter 130, and the second detector 351 are optional. As is shown in FIG. 1A, the beamsplitter 30 and 130 and the first half wave plate 301, a second half wave plate 302, a quarter wave plate 311, a second beamsplitter 130, and a second detector 351 are positioned on top of the housing-window 415 and are outside the vacuum in the housing 412.

If the laser power and the temperature of the gas reference cell 40 are well controlled, the single detector 350 mounted on the first beamsplitter 30 is the only optical detector required. The gas reference cell temperature can be controlled via a resistive temperature sensor 505 and the laser power can be separately servo'd by the electro-optical (EO) based intensity servo 325. If the laser power is subject to drift, a second detector 130 (as shown in FIG. 1A) is implemented to control the laser power fluctuations. The portion of the laser light falling directly on the second detector 130 is used to monitor laser power fluctuations so that their effect can be subtracted out of the feedback signal 50 for laser frequency by subtraction electronics 12.

The second half wave plate 302 is positioned at an output face 30B of the first beamsplitter 30. The second half wave plate 302 has a third fast axis. The optical beam 29 (i.e., the second portion of the optical beam 20) is transmitted through the second half wave plate 302 and is incident on the second beamsplitter 130. The second beamsplitter 130 reflects a portion of the optical beam 29 (also referred to herein as a third portion of the input optical beam 20) as optical beam 28 toward the second detector 351. The second beamsplitter 130 transmits a portion of the optical beam 29 (also referred to herein as a fourth portion of the input optical beam 20) as optical beam 29' toward the external component outside of the spectroscopic assembly 5.

The orientation of the third fast axis of the half wave plate 302 with reference to the polarization of the optical beam 29 is used to control the ratio of fourth portion of the input optical beam 20 (e.g., the intensity of the optical beam 29') to the third portion of the input optical beam 20 (e.g., the intensity of the optical beam 28). Thus, the orientation of the third fast axis with reference to the polarization of the optical beam 29 controls the relative intensity of the optical beam 29' and the optical beam 28. In one implementation of this embodiment, the second beamsplitter 130 reflects 10% of the optical beam 29 and transmits 90% of the optical beam 29 so the ratio of the fourth portion to the third portion of is 90/10.

The second detector 351 is positioned to receive the optical beam 28 that is reflected from the second beamsplitter 130. The second detector 351 measures fluctuations in the amplitude of the optical beam 28 (third portion of the optical beam 20) so that the feedback signal sent to the laser driver 14 reduces intensity fluctuations of the input optical beam 20 emitted by the laser 10. In this manner, intensity fluctuations are removed from the feedback signal used to stabilize the frequency of the laser 10. The outputs from the first and second detectors 350 and 351 are input to subtraction electronics 12. The subtraction electronics 12 normalizes the spectroscopic signal 50 that is sent to the laser driver 14 via link 13. A change in the light level (intensity) at the first detector may be due to a change in laser frequency or a change in laser power. Without a second detector, the servo system always tries to change the laser frequency to restore the light level. If the change in light level was not due to a change in frequency, however, this servo-correction actually drags the frequency away from the desired operating frequency. To avoid this, the signal on the second detector is subtracted from the signal on the first detector (with an appropriate amount of gain at each subtractor input). In this case, if the laser power changes, the light level on both detectors changes by the same amount, and the subtracted signal does not change. However, if the laser frequency changes, the light level on the first detector changes and the light level on the second detector does not change. The level of the subtracted signal therefore changes, and the servo (correctly) adjusts the laser frequency to restore the subtracted signal to its previous value. It is to be understood that this normalization could also be accomplished by dividing one signal by another so that the ratio is insensitive to changes in both, rather than by subtracting the two signals.

In one implementation of this embodiment, the gas reference cell 40 is approximately 1 mm on a side. In one implementation of this embodiment, the beamsplitter 30 is a 90-10 beam cube. In another implementation of this embodiment, the beamsplitter 30 is an 80-20 beam cube. In another implementation of this embodiment, the beamsplitter 130 is a 90-10 beam cube. Other splitting ratios for the beamsplitters 30 and 130 are possible. In some implementations the beamsplitter is a polarizing beamsplitter and the ratio is controlled by the polarization of the light, which can be set by a half wave plate. The half wave plate is not necessary if the beamsplitter is non-polarizing, with a fixed ratio, or if it is polarizing but the polarization of the light has already been set to the desired orientation by other means.

In yet another implementation of this embodiment, the gas 41 is heated to 60 degrees Celsius. The gas reference cell 40 includes one of rubidium gas, cesium gas, acetylene gas, sodium gas, or potassium gas, or another gas which has a saturated absorption spectrum at a laser-accessible wavelength. The gas reference cell 40 contains the relevant vapor at low pressure, with minimal partial pressure (such as less than 0.1 atmosphere) due to other gasses (including commonly used "buffer gasses" such as nitrogen and argon).

In one implementation of this embodiment, the optical beam 26 incident on the first detector 350 is provided by reflection from an uncoated glass window (e.g., second optically-transparent window 46) of the gas reference cell 40. In another implementation of this embodiment, the second optically-transparent window 46 is coated to achieve a different reflectivity. In yet another implementation of this embodiment, additional elements (such as, a mirror or wave plates) are incorporated into the package on the side of the gas reference cell 40 opposite the housing-window 415.

Figure 2:
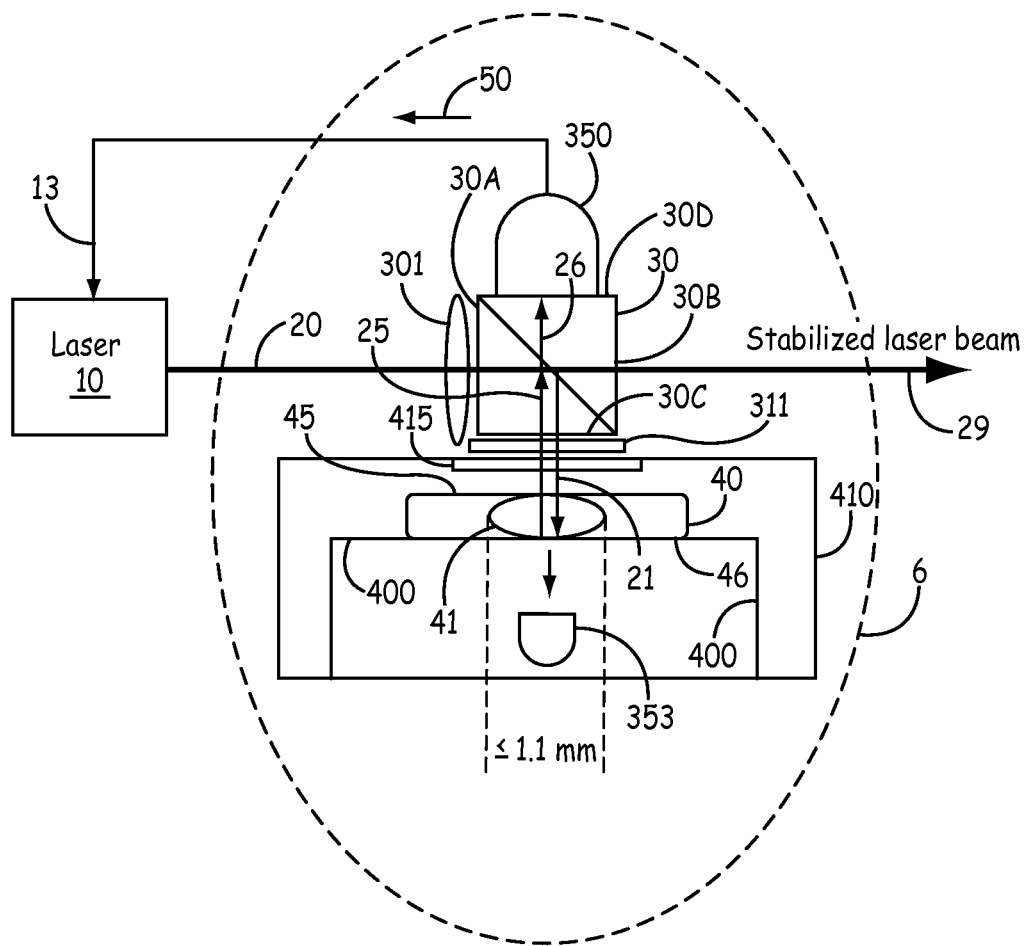
FIGS. 2-5 are block diagrams of embodiments of spectroscopy assemblies configured to stabilize a laser beam in accordance with the present invention.

FIGS. 2-5 are block diagrams of embodiments of spectroscopy assemblies configured to stabilize a laser beam in accordance with the present invention. FIG. 2 is a block diagram of the spectroscopy assembly 6 aligned to provide feedback to lock the frequency of the laser 10 so that a stabilized laser beam 29 is output from the spectroscopic assembly 6. The spectroscopic assembly 6 differs from the spectroscopic assembly 5 of FIG. 1A in that there is no second half wave plate 302, second beamsplitter 130, second detector 351, and subtraction electronics 12. There is no electro-optical (EO) based intensity servo 325 positioned at the input to the spectroscopic assembly 6 and an external component 160 is not shown. The laser driver 14 and the current sources 670 and 671 connected to leads 650-653 shown in FIG. 1A are not shown in FIG. 2. As shown in FIG. 2, the beamsplitter 30 is a cube beamsplitter 30 with faces 30A, 30B, 30C, and 30D. Face 30A opposes 30B and face 30C opposes face 30D. The input optical beam 20 is input to the spectroscopic assembly 6 via face 30A. The detector 350 is positioned adjacent to face 30D of the beamsplitter 30. A half wave plate 301 positioned adjacent to face 30A of the cube beamsplitter 30. A quarter wave plate 311 is positioned between the face 30C of the cube beamsplitter 30 and the transparent window 415 of the housing 410. The beamsplitter 30, the half wave plate 301, quarter wave plate 311, the gas reference cell 40, the thermal isolation platform 400, and the housing 410 are functional as described above with reference to FIGS. 1A-1B.

FIG. 2 also shows an optional monitor detector 353. In this configuration, the monitor detector 353 is adjacent to the second optically-transparent window 46 and monitors intensity of the reflected portion 21 of the input optical beam 20 transmitted through the gas 41 in the gas reference cell 40. Specifically, the monitor detector 353 receives the light 21, which has passed one time through the first optically-transparent window 45, the gas 41, and the second optically-transparent window 46 in order to monitor the absorption of the gas 41 in the gas reference cell 40. The monitor detector 353 is useful when the temperature of the gas reference cell 40 is not well controlled. The spectroscopic assembly 6 stabilizes an input optical beam 20 emitted by a laser 10 (FIG. 1A). In one implementation of this embodiment, the spectroscopic assembly 6 is a miniature spectroscopic assembly 6 and the gas reference cell 40 is a miniature gas reference cell 40.

This configuration of the spectroscopic assembly 6 is compact and requires low power to heat the gas 41 in the gas reference cell 40. In one implementation of this embodiment, the components of the spectroscopic assembly 6 (i.e., the beamsplitter 30, the detector 350, the half wave plate 301, and the quarter wave plate 311) are held in position with the housing 410 by mechanical features, adhesives, and/or housing structures as is understandable to one skilled in the art upon reading and understanding this document.

Figure 3:
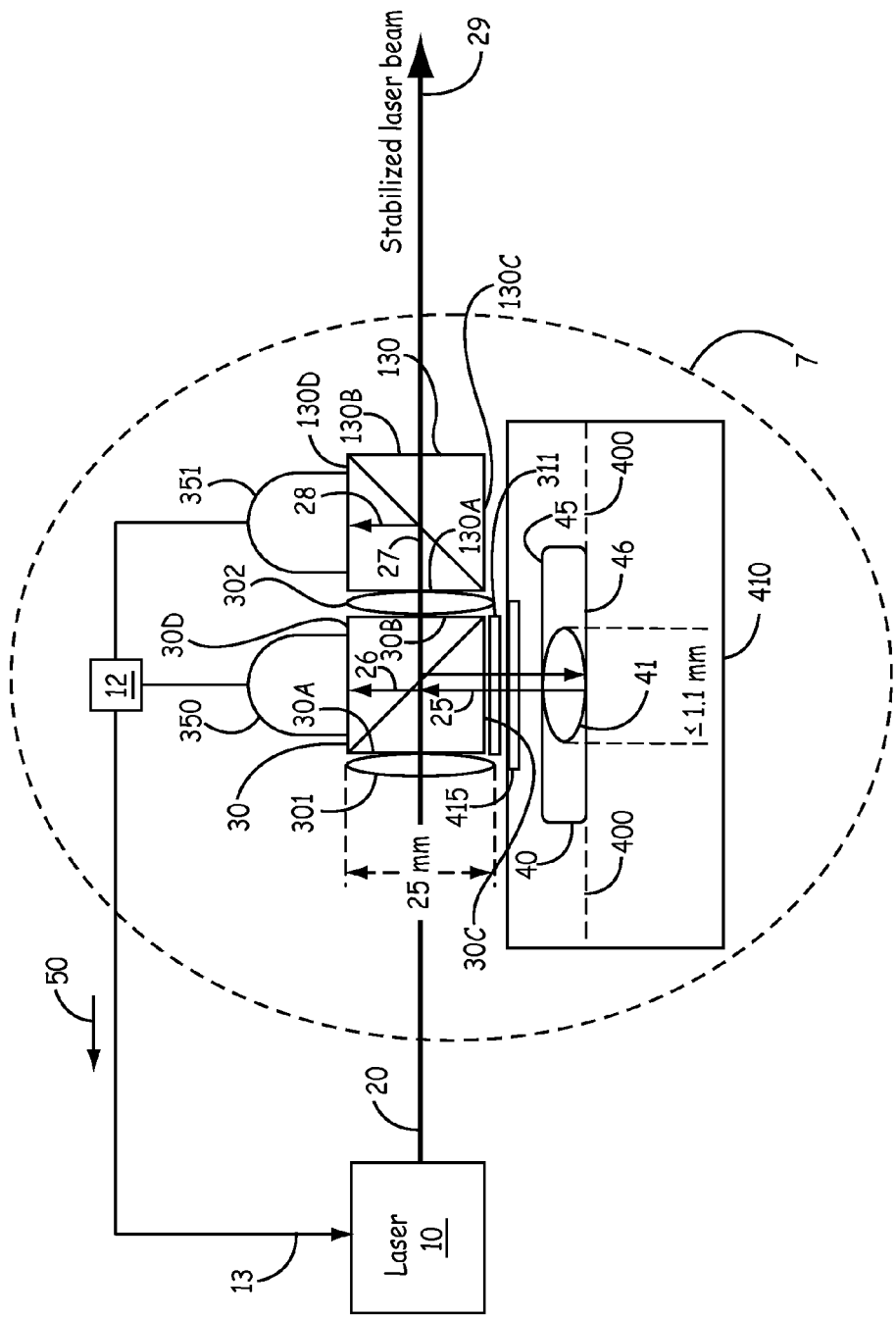

FIG. 3 is a block diagram of the spectroscopy assembly 7 aligned to provide feedback to lock the frequency of the laser 10 so that a stabilized laser beam 29 is output from the spectroscopic assembly 7. There is no electro-optical (EO) based intensity servo 325 positioned at the input to the spectroscopic assembly 7 and an external component 160 is not shown. The laser driver 14 and the current sources 670 and 671 shown in FIG. 1A are not shown in FIG. 3. The spectroscopic assembly 7 is a compact version of the spectroscopic assembly 5 of FIG. 1A.

As shown in FIG. 3, the first beamsplitter 30 is a first cube beamsplitter 30 with faces 30A, 30B, 30C, and 30D. The second beamsplitter 130 is a second cube beamsplitter 130 with faces 130A, 130B, 130C, and 130D. Face 130A opposes 130B and face 130C opposes face 130D. The first detector 350 is positioned adjacent to the face 30D of the beamsplitter 30. The second detector 351 is positioned adjacent to the face 130D of the beamsplitter 130. The first half wave plate 301 is positioned adjacent to the face 30A of the first cube beamsplitter 30. The second half wave plate 302 is positioned between the face 30B of the first cube beamsplitter 30 and the face 130A of the second cube beamsplitter 130. A quarter wave plate 311 is positioned between the face 30C of the cube beamsplitter 30 and the transparent window 415 of the housing 410. The face 130C is positioned adjacent to the housing 410. The components of the spectroscopic assembly 7 are functional to stabilize the laser 10 as described above with reference to FIGS. 1A-1B. This configuration of the spectroscopic assembly 7 is compact and requires low power to heat the gas 41 in the gas reference cell 40. In one implementation of this embodiment, the components of the spectroscopic assembly 7 (i.e., the first beamsplitter 30, the second beamsplitter 130, the first detector 350, the second detector 351, the first half wave plate 301, the quarter wave plate 311, and the second half wave plate 302) are held in position with the housing 410 by mechanical features, adhesives, and/or housing structures as is understandable to one skilled in the art upon reading and understanding this document.

Figure 4:
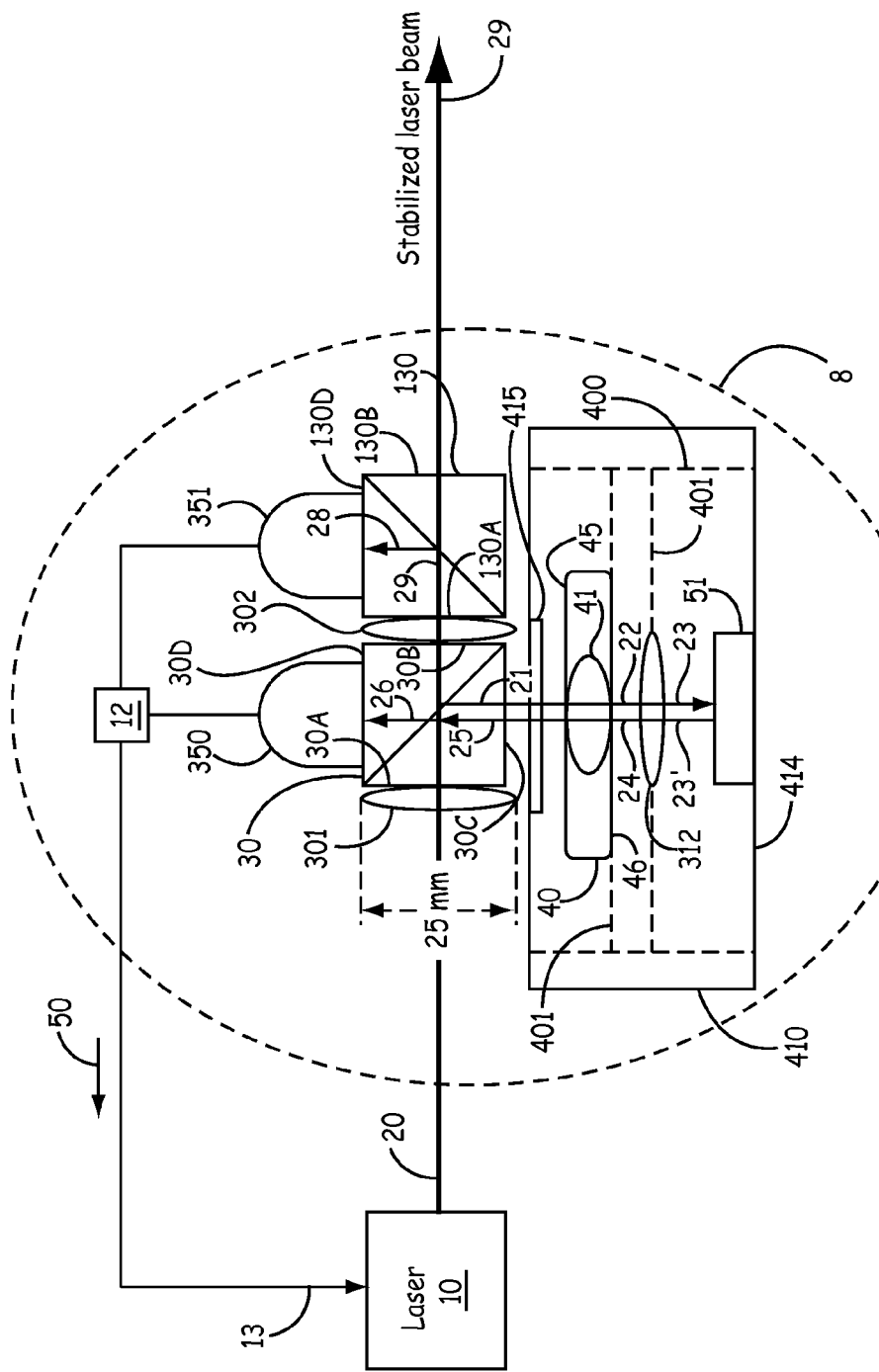

FIG. 4 is a block diagram of the spectroscopy assembly 8 aligned to provide feedback to lock the frequency of the laser 10 so that a stabilized laser beam 29 is output from the spectroscopic assembly 8. There is no electro-optical (EO) based intensity servo 325 positioned at the input to the spectroscopic assembly 8 and the external component 160 is not shown. The laser driver 14 and the current sources 670 and 671 shown in FIG. 1A are not shown in FIG. 4.

As shown in FIG. 4, the first detector is positioned adjacent to face 30D. The second detector 351 is positioned adjacent to face 130D. The first half wave plate 301 is positioned adjacent to the face 30A of the first cube beamsplitter 30. The second half wave plate 302 is positioned between the face 30B of the first cube beamsplitter 30 and the face 130A of the second cube beamsplitter 130. The face 30C is positioned adjacent to the transparent window 415 of the housing 410. The face 130C is positioned adjacent to the housing 410.

The first half wave plate 301 has a fast axis (referred to herein as a first fast axis). The first half wave plate 301 is positioned at an input face 30A of the polarization beamsplitter 30. The orientation of the first fast axis with reference to the polarization of the input optical beam 20 is used to control the ratio of second portion of the optical beam 20 (e.g., the intensity of the optical beam 29) to the first portion of the optical beam (e.g., the intensity of the optical beam 21).

As shown in FIG. 4, the second optically-transparent window 46 of the gas reference cell 40 is positioned between a reflective surface 51 and the first optically-transparent window 45 of the gas reference cell 40. The reflective surface 51 is positioned on a surface 414 of the housing 410. The surface 414 opposes the transparent window 415 of the housing 410. In one implementation of this embodiment, the reflective surface 51 is a mirror. In another implementation of this embodiment, reflective surface 51 is a partially reflective surface. In yet another implementation of this embodiment, the first optically-transparent window 45 and second optically-transparent window 46 are anti-reflection coated.

The spectroscopic assembly 8 includes a quarter wave plate 312 that has a fast axis (referred to herein as a second fast axis). The quarter wave plate 312 is positioned between the second optically-transparent window 46 of the gas reference cell 40 and the reflective surface 51. The second fast axis of the quarter wave plate 312 is orientated with reference to a polarization of the reflected portion 21 of the input optical beam 20 so that a first polarization of the optical beam 22 propagating through the gas 41 a first time is orthogonal to a second polarization of the optical 24 propagating through the gas 41 a second time. The quarter wave plate 312 is operably positioned in the thermal isolation platform 400.

The components of the spectroscopic assembly 8 are functional to stabilize the laser 10 as described above with reference to FIGS. 1A-1B. In one implementation of this embodiment, the components of the spectroscopic assembly 8 (i.e., the first beamsplitter 30, the second beamsplitter 130, the first detector 350, the second detector 351, the first half wave plate 301, the quarter wave plate 312, and the second half wave plate 302) are held in position with the housing 410 by mechanical features, adhesives, and/or housing structures as is understandable to one skilled in the art upon reading and understanding this document.

Figure 5:
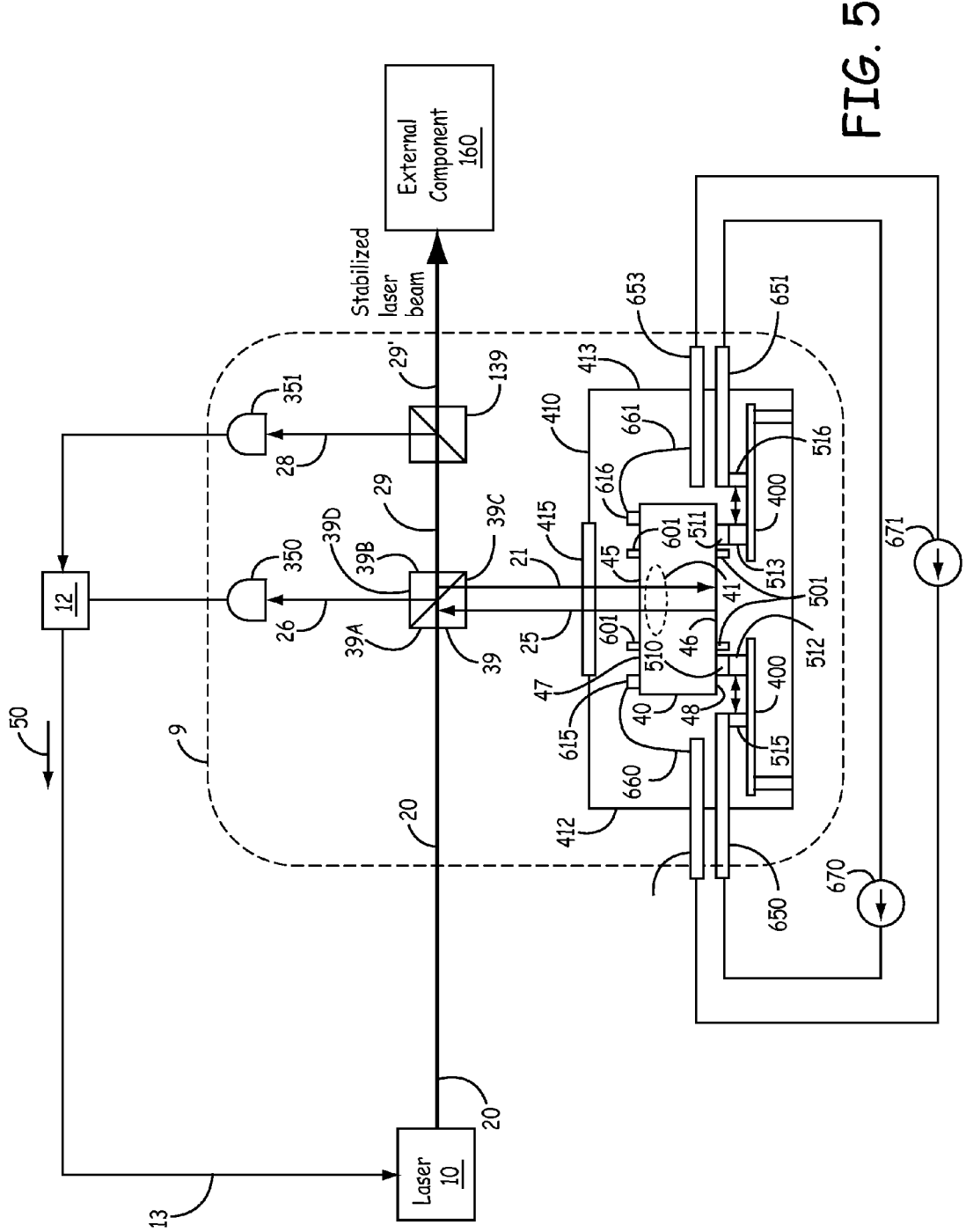

FIG. 5 is a block diagram of an embodiment of a spectroscopy assembly 9, a laser 10, and an external component 160 in accordance with the present invention. The spectroscopy assembly 9 shown in FIG. 5 is aligned to provide feedback to lock the laser 10 to a selected frequency. The spectroscopic assembly 9 includes a housing 410, a thermal isolation platform 400, and a gas reference cell 40, which encases a gas 41. The beamsplitter 39 and the second beamsplitter 139 are not polarization beamsplitters. The beamsplitter 39 transmits a first percentage of the incident optical beam 20 and reflects a second percentage of the incident optical beam 20. Likewise, beamsplitter 139 transmits a third percentage of the incident optical beam 29 and reflects a fourth percentage of the incident optical beam 29. In one implementation of this embodiment, the first and third percentages are equal to each other and the second and fourth percentages are equal to each other. The first and second percentages sum to approximately hundred percent. The third and fourth percentages sum to approximately hundred percent. A small portion of the optical beam 20 may be absorbed by the coatings in the beamsplitters 39 and 139.

Since the beamsplitters 39 and 139 are not polarization beamsplitters, there is no need for the first half wave plate 301, the second half wave plate 302, and the quarter wave plate 311 to orient the polarization of the optical beams. Thus, the spectroscopy assembly 9 differs from the spectroscopy assembly 5 of FIG. 1 in that there is no first half wave plate 301, second half wave plate 302, and quarter wave plate 311. There is no electro-optical (EO) based intensity servo 325 shown in the spectroscopy assembly 9, but an electro-optical (EO) based intensity servo 325 may be optionally included in the spectroscopy assembly 9.

The function of the spectroscopic assembly 9 is the same as the function of the spectroscopic assembly 5 shown in FIG. 1A. The housing 410 and the gas reference cell 40 in the spectroscopic assembly 9 are similar in structure and function to the housing 410 and gas reference cell 40 in FIG. 5. In one implementation of this embodiment, the spectroscopic assembly 9 does not include the second beamsplitter 139.

Figure 6:
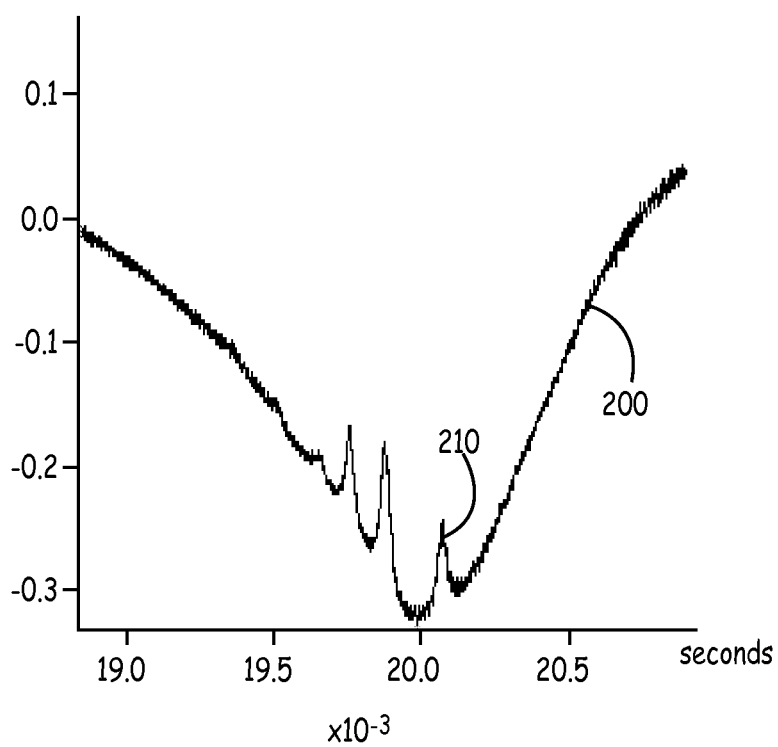
FIG. 6 shows a spectroscopy signal derived from a miniature vapor cell to be used for the laser frequency stabilization in accordance with the present invention.

FIG. 6 shows a spectroscopy signal 200 derived from a miniature gas reference cell 40 (vapor cell) of Rubidium gas to be used for the laser frequency stabilization. The plot shown in FIG. 6 is generated as the laser frequency changes in time so the vertical axis is in Volts and the horizontal axis is time (seconds). The first trace shows the entire F=2 saturated absorption trace scanned approximately 1 GHz over the Doppler broadened absorption profile. In this exemplary case, the Rubidium gas has a peak 210 at 384.2292416 THz. The peak 210 is the peak to which the laser 10 will be locked. The peak 210 is the F=2→3 cycling transition and is on the order of 10's of MHz wide. If the gas 41 is formed from other elements, then other peaks can be selected for locking In one implementation of this embodiment, the laser 10 is locked at a frequency that is 10-15 MHz lower in frequency than the peak 210, i.e., on the side of the peak 210.

Figure 7:
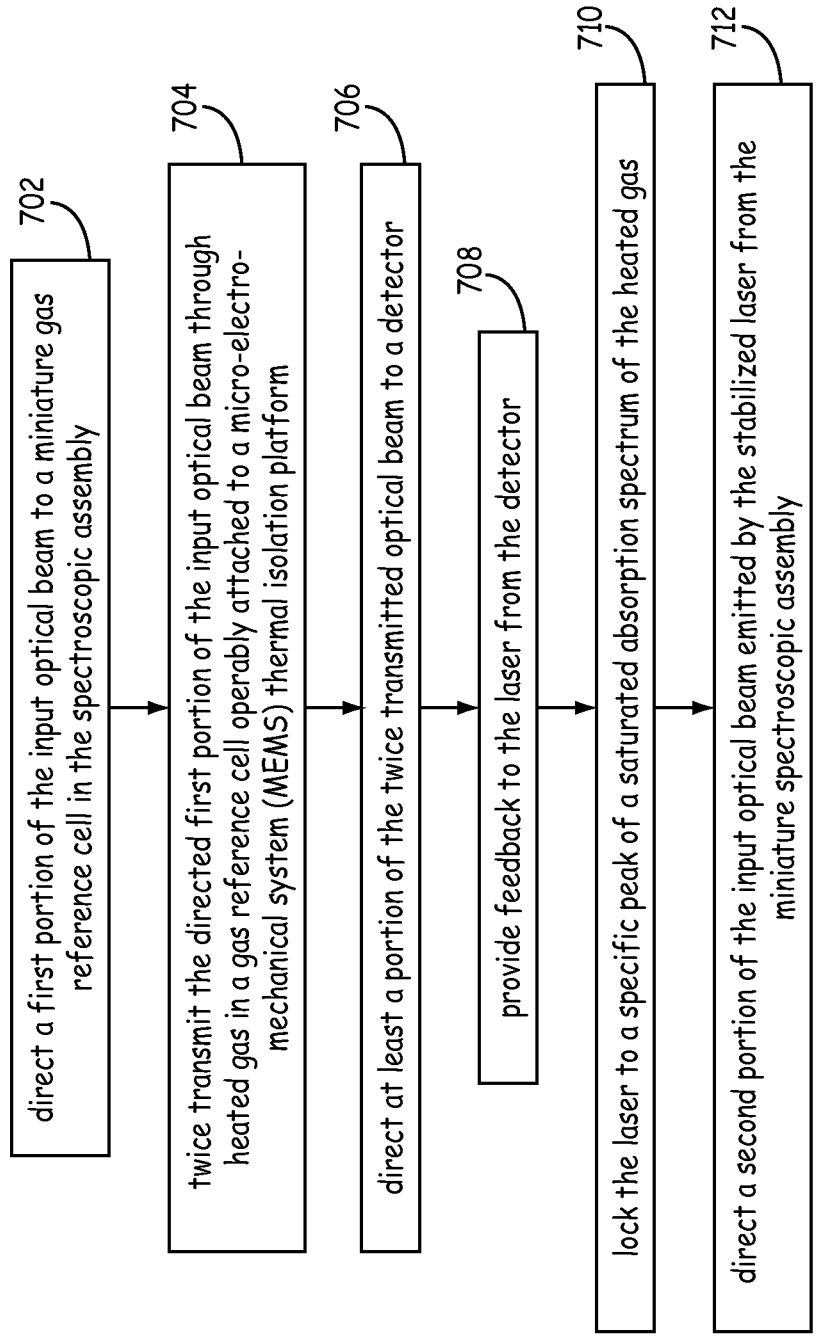
FIG. 7 is a flow diagram of one embodiment of a method to stabilize an optical beam output from a laser in accordance with the present invention.

FIG. 7 is a flow diagram of one embodiment of a method 700 to stabilize an optical beam output from a laser in accordance with the present invention. In one implementation of this embodiment, method 700 is implemented to stabilize an optical beam output from the laser 10 in a miniature spectroscopic assembly in which the gas reference cell 40 is one of the miniature gas reference cells 140 fabricated on wafer 700. In one implementation of this embodiment, an input optical beam 20 is stabilized as an output optical beam 29 in one of the spectroscopic assemblies 5, 6, 7, or 8 as described above with reference to FIGS. 1A-4. The method 700 is described with reference to the spectroscopic assembly 8 shown in FIG. 4 although it is to be understood that method 700 can be implemented using other embodiments of the spectroscopic assembly as is understandable by one skilled in the art who reads this document. Likewise, the method 700 is described with reference to a miniature gas reference cell 40 although it is to be understood that method 700 can be implemented using gas reference cells that are not miniature in size.

At block 702, a first portion of the input optical beam 20 is directed to a miniature gas reference cell 40 in the spectroscopic assembly 8. The first portion of the input optical beam 20 is the portion of the input optical beam 20 reflected by the beamsplitter 30. At block 704, the directed first portion of the input optical beam 20 (i.e., optical beam 21) is twice transmitted through heated gas 41 in a miniature gas reference cell 40 that is operably attached to a micro-electro-mechanical system (MEMS) thermal isolation platform 400. The miniature gas reference cell 40 is in a housing 410. A vacuum is created in the housing 410. At block 706, at least a portion of the twice transmitted optical beam 25 is directed to a detector 350.

At block 708, feedback (signal 50) is provided to the laser 10 from the detector 350. At block 710, the laser 10 is locked a specific peak (e.g., peak 210 shown in FIG. 7) of a saturation absorption spectrum 200 (FIG. 7) of the heated gas 41. At block 712, a second portion of the input optical beam 20 emitted by the stabilized laser 10 (optical beam 29) is directed from the miniature spectroscopic assembly 5. The second portion of the input optical beam 20 is that portion of the input optical beam 20 that is transmitted through the beamsplitter 30.

In one implementation of this embodiment, of method 700, a third portion of the second portion of the input optical beam (e.g., optical beam 28) is directed to a second detector 351. An amplitude of the third portion of the optical beam (e.g., optical beam 28) is measured and the amplitude fluctuations of the optical beam 28 are subtracted (using subtraction electronics 12) from the feedback signal 50 provided to the laser 10. In another implementation of this embodiment, an electro-optical-based intensity servo 325 is positioned in the optical path of the optical beam 20 to reduce laser relative intensity noise.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention. Therefore, it is manifestly intended that this invention be limited only by the claims and the equivalents thereof.

What is claimed is:

1. A spectroscopic assembly, comprising:
   a thermal isolation platform;
   a gas reference cell encasing a gas and attached to the thermal isolation platform, the gas reference cell having at least one optically-transparent window; and
   at least one heater configured to raise a temperature of the encased gas, wherein the at least one heater is patterned on one of: the gas reference cell or the thermal isolation platform, wherein when a beam splitter is configured to reflect a portion of an input optical beam emitted by a laser to be incident on the at least one optically-transparent window of the gas reference cell, and an at least partial reflective surface is configured to reflect the reflected portion, the reflected portion of the input optical beam is twice transmitted through the gas, and when a detector is configured to receive the optical beam twice transmitted through the gas, a feedback signal is provided to the laser to stabilize the laser.

2. The spectroscopic assembly of claim 1, further comprising:
   a housing having a transparent window, the housing configured for sealing the thermal isolation platform and the gas reference cell under vacuum, the transparent window being positioned to transmit the reflected portion of the input optical beam into the gas reference cell and positioned to transmit the optical beam twice transmitted through the gas to the beamsplitter.

3. The spectroscopic assembly of claim 2, wherein the at least one optically-transparent window of the gas reference cell comprises:
   a first optically-transparent window on a first surface of the gas reference cell; and
   a second optically-transparent window on a second surface of the gas reference cell, the second surface opposing the first surface.

4. The spectroscopic assembly of claim 3, wherein the at least one heater is patterned on at least one of the first optically-transparent window, the second optically-transparent window, a first surface of the gas reference cell, a second surface of the gas reference cell, a portion of the thermal isolation platform adjacent to the first optically-transparent window, and a portion of the thermal isolation platform adjacent to the second optically-transparent window.

5. The spectroscopic assembly of claim 1, wherein the beamsplitter is a polarization beamsplitter, the spectroscopic assembly further comprising:
   at least one half wave plate configured to orientate a polarization of the input optical beam, wherein the reflected portion of the input optical beam depends on the orientated polarization of the input optical beam; and
   at least one quarter wave plate configured to control the polarization of the reflected portion of the input optical beam and to control the polarization of the optical beam twice transmitted through the gas.

6. A spectroscopic assembly to stabilize an optical beam, the spectroscopic assembly comprising:
   a gas reference cell encasing a gas and attached to a thermal isolation platform, the gas reference cell having a first optically-transparent window and a second optically-transparent window;
   at least one heater to raise a temperature of the encased gas, wherein the at least one heater is patterned on one of: the gas reference cell or the thermal isolation platform;
   a beam splitter configured to reflect a portion of an input optical beam emitted by a laser to be incident on the first optically-transparent window of the gas reference cell, wherein the reflected portion of the input optical beam is transmitted through the gas, reflected from an at least partially reflective surface, and retransmitted through the gas;
   and a detector configured to receive the optical beam twice transmitted through the gas, wherein the optical beam twice transmitted through the gas is locked to a specific peak of a saturated absorption spectrum of the heated gas, wherein the detector is configured to provide a feedback signal to stabilize the frequency of the optical beam emitted by the laser.

7. The spectroscopic assembly of claim 6, wherein the at least one heater is patterned on at least one of the first optically-transparent window, the second optically-transparent window, a first surface of the gas reference cell, a second surface of the gas reference cell, a portion of a thermal isolation platform adjacent to the first optically-transparent window, and a portion of the thermal isolation platform adjacent to the second optically-transparent window.

8. The spectroscopic assembly of claim 6, further comprising a monitor detector adjacent to the second optically-transparent window to monitor intensity of the reflected portion of the input optical beam transmitted once through the gas.

9. The spectroscopic assembly of claim 6, wherein the beamsplitter is a polarization beamsplitter, the spectroscopic assembly further comprising:
   a half wave plate having a fast axis, the half wave plate positioned at an input face of the polarization beamsplitter, wherein an orientation of the fast axis with reference to a polarization of the input optical beam is used to control a ratio of a second portion of the optical beam to a first portion of the optical beam.

10. The spectroscopic assembly of claim 9, wherein the fast axis of the half wave plate is a first fast axis, and wherein the at least partially reflective surface is the second optically-transparent window, the spectroscopic assembly further comprising, a quarter wave plate having a second fast axis, the quarter wave plate positioned between an output face of the polarization beam splitter and the first optically-transparent window of the gas reference cell, wherein an orientation of the second fast axis with reference to a polarization of the reflected portion of the input optical beam controls the polarization of the optical beam twice transmitted through the gas.

11. The spectroscopic assembly of claim 9, wherein the fast axis of the half wave plate is a first fast axis, and wherein the second optically-transparent window is positioned between the at least partially reflective surface and the first optically-transparent window, the spectroscopic assembly further comprising:
a quarter wave plate having a second fast axis, the quarter wave plate positioned between the second optically-transparent window of the gas reference cell and the at least partially reflective surface, wherein the second fast axis is orientated with reference to a polarization of the reflected portion of the input optical beam so that a first polarization of the optical beam propagating through the gas a first time is orthogonal to a second polarization of the optical beam propagating through the gas a second time.

12. The spectroscopic assembly of claim 6, wherein the beamsplitter is a first beamsplitter, and the detector is a first detector, the spectroscopic assembly further comprising:
a first half wave plate having a first fast axis, the first half wave plate positioned at an input face of the polarization beamsplitter, wherein an orientation of the first fast axis with reference to a polarization of the input optical beam is used to a ratio of a second portion to a first portion of the optical beam;
a second half wave plate positioned at an output face of the first beamsplitter, wherein the second portion of the optical beam is transmitted through the second half wave plate;
a second beamsplitter to reflect a third portion of the second portion of the optical beam transmitted through the second half wave plate and to transmit a fourth portion of the second portion of the optical beam transmitted through the second half wave plate, wherein an orientation of the second fast axis with reference to a polarization of the second portion of the optical beam is used to control the ratio of fourth portion to the third portion of the optical beam; and
a second detector to receive the reflected third portion of the optical beam, wherein the second detector is configured to measure fluctuations in the amplitude of the third portion of the optical beam so that the feedback signal reduces intensity fluctuations of the input optical beam emitted by the laser.

13. The spectroscopic assembly of claim 6, further comprising:
a housing having a transparent window, the housing configured for sealing the thermal isolation platform and the gas reference cell under vacuum, the transparent window being positioned to transmit the reflected portion of the input optical beam into the gas reference cell and positioned to transmit the optical beam twice transmitted through the gas to the beamsplitter.

14. The spectroscopic assembly of claim 6, further comprising:
a temperature sensor patterned on at least one of the first optically-transparent window, the second optically-transparent window, a first surface of the gas reference cell, a second surface of the gas reference cell, a portion of the thermal isolation platform adjacent to the first optically-transparent window, and a portion of the thermal isolation platform adjacent to the second optically-transparent window.

15. The spectroscopic assembly of claim 6, wherein the thermal isolation platform is a micro-electro-mechanical system (MEMS) thermal isolation platform and the gas reference cell is a miniature gas reference cell.

16. The spectroscopic assembly of claim 6, further comprising an electro-optical-based intensity servo configured to reduce laser relative intensity noise of the input optical beam emitted by the laser.

17. A method to stabilize an input optical beam emitted by a laser in a miniature spectroscopic assembly, the method comprising:
directing a first portion of the input optical beam to a miniature gas reference cell in the miniature spectroscopic assembly through at least one optically-transparent window of the gas miniature gas reference cell;
twice transmitting the directed first portion of the input optical beam, using an at least partially reflective surface configured to reflect at least a portion of the directed first portion of the input optical beam, through heated gas in a gas reference cell operably attached to a micro-electro-mechanical system (MEMS) thermal isolation platform, wherein at least one heater is patterned on one of: the miniature gas reference cell or the MEMS thermal isolation platform; directing at least a portion of the twice transmitted optical beam to a detector; providing feedback to the laser from the detector; locking the laser to a specific peak of a saturated absorption spectrum of the heated gas in order to stabilize a frequency of the input optical beam emitted by the laser; and directing a second portion of the input optical beam emitted by the stabilized laser from the miniature spectroscopic assembly.

18. The method of claim 17, further comprising:
enclosing the miniature gas reference cell in a housing; and creating a vacuum in the housing.

19. The method of claim 17, wherein the detector is a first detector, the method further comprising:
directing a third portion of the second portion of the input optical beam to a second detector;
measuring an amplitude of the third portion of the optical beam; and
subtracting amplitude fluctuations of the optical beam from the feedback signal provided to the laser.

20. The method of claim 17, further comprising:
positioning an electro-optical-based intensity servo in the optical path of the optical beam to reduce laser relative intensity noise.

* * * * *